United States Patent
Howard

(10) Patent No.: US 12,076,166 B2
(45) Date of Patent: Sep. 3, 2024

(54) NEURAL OSCILLATION MONITORING SYSTEM

(71) Applicant: Newton Howard, Providence, RI (US)

(72) Inventor: Newton Howard, Providence, RI (US)

(*) Notice: Subject to any disclaimer, the term of this patent is extended or adjusted under 35 U.S.C. 154(b) by 0 days.

(21) Appl. No.: 15/257,019

(22) Filed: Sep. 6, 2016

(65) Prior Publication Data
US 2017/0065229 A1 Mar. 9, 2017

Related U.S. Application Data

(60) Provisional application No. 62/214,443, filed on Sep. 4, 2015.

(51) Int. Cl.
| | | |
|---|---|---|
| A61B 5/00 | (2006.01) | |
| A61B 5/16 | (2006.01) | |
| A61B 5/316 | (2021.01) | |
| A61B 5/369 | (2021.01) | |

(52) U.S. Cl.
CPC ............ *A61B 5/7267* (2013.01); *A61B 5/316* (2021.01); *A61B 5/369* (2021.01); *A61B 5/165* (2013.01); *A61B 5/4824* (2013.01); *A61B 5/7257* (2013.01); *A61B 5/726* (2013.01)

(58) Field of Classification Search
None
See application file for complete search history.

(56) References Cited

U.S. PATENT DOCUMENTS

| | | |
|---|---|---|
| 6,159,015 A | 12/2000 | Buffington et al. |
| 6,338,628 B1 | 1/2002 | Smith |
| 2003/0040080 A1 | 2/2003 | Miesenbock et al. |
| 2003/0195584 A1 | 10/2003 | Dawson |
| 2004/0019370 A1 | 1/2004 | Gliner et al. |
| 2004/0186719 A1 | 9/2004 | Polanyi et al. |
| 2005/0118558 A1 | 6/2005 | Wallis et al. |
| 2005/0142524 A1 | 6/2005 | Simon et al. |
| 2005/0250082 A1 | 11/2005 | Baldwin et al. |
| 2006/0004279 A1 | 1/2006 | Ikeda et al. |
| 2006/0095251 A1 | 5/2006 | Shaw |
| 2007/0117073 A1 | 5/2007 | Walker et al. |
| 2007/0225674 A1 | 9/2007 | Molnar et al. |
| 2009/0157389 A1 | 6/2009 | Shaw |
| 2011/0015538 A1 | 1/2011 | Matthews, Jr. |
| 2011/0027765 A1 | 2/2011 | Nader |
| 2012/0219934 A1 | 8/2012 | Nakane et al. |

OTHER PUBLICATIONS

Lotte, Fabien, Laurent Bougrain, and Maureen Clerc. "Electroencephalography (EEG)-based brain-computer interfaces." (2015): 44.*

Alotaiby, Turky, et al. "A review of channel selection algorithms for EEG signal processing." EURASIP Journal on Advances in Signal Processing 2015 (2015): 1-21.*
Non-final Office Action dated Feb. 27, 2013 issued in parent U.S. Appl. No. 13/083,352.
News Bias Explored; Word Choice Buffet: All You Can Eat. [Jun. 30, 2009], {Retrieved Feb. 19, 2013 U <http://www.umich.edu/-newsbias/wcact.html>, [Retrieved from Internet Archive Wayback Machine <URL: http://web.archive.org/web/20090630024420/http://www.umich.edu/-newsbias/wcact.html».
Notification of Transmittal of International Search Report and the Written Opinion dated Jun. 21, 2011 received in International Application No. PCT/US2011/031319.
Notification Concerning Transmittal of Copy of International Preliminary Report on Patentability dated Oct. 18, 2012 received in International Application No. PCT/US2011/031319.
Non-final Office Action dated Jan. 15, 2016 issued in U.S. Appl. No. 12/880,042.
Amendment filed Dec. 3, 2015 in U.S. Appl. No. 12/880,042.
Final Office Action dated Jun. 4, 2015 issued in U.S. Appl. No. 12/880,042.
Amendment filed Feb. 10, 2015 in U.S. Appl. No. 12/880,042.
Non-final Office Action dated Sep. 10, 2014 issued in U.S. Appl. No. 12/880,042.
Amendment filed Jul. 30, 2014 in U.S. Appl. No. 12/880,042.
Final Office Action dated Jan. 30, 2014 issued in U.S. Appl. No. 12/880,042.
Response filed Oct. 18, 2013 in U.S. Appl. No. 12/880,042.
Non-final Office Action dated Apr. 18, 2014 issued in U.S. Appl. No. 12/880,042.
H.D. Block, The Perceptron: A Model for Brain Functioning. I*, Reviews of Modern Physics, vol. 34, No. 1 dated Jan. 1962 pp. 123-135.
Brian S. Blais, et al., The role of presynaptic activity in monocular deprivation: Comparison of homosynaptic and heterosynaptic mechanisms, Proc. Natl. Acad. Sci, USA, vol. 96, pp. 1083-1087, Feb. 1999.
Sydney Lamb—lamb@rice.edu, Wenzao Ursuline College of Languages, Kaohsiung, Taiwan, On the Neurocognitive Basis of Language, pp. 1-156, Nov. 12, 2010.

(Continued)

*Primary Examiner* — G. Steven Vanni
(74) *Attorney, Agent, or Firm* — Michael A. Schwartz

(57) ABSTRACT

Embodiments of the present invention may provide automated techniques for signal analysis that may continuously provide up-to-date results that link EEG and behaviors that are important for daily activities. Such techniques may provide automation, objectivity, real-time monitoring and portability. In an embodiment of the present invention, a computer-implemented method for monitoring neural activity may comprise receiving data representing at least one signal representing neural activity of a test subject, pre-processing the received data by performing at least one of band-pass filtering, artifact removal, identifying common spatial patterns, and temporally segmentation, processing the pre-processed data by performing at least one of time domain processing, frequency domain processing, and time-frequency domain processing, generating a machine learning model using the processed data as a training dataset, and outputting a characterization of the neural activity based on the machine learning model.

19 Claims, 8 Drawing Sheets

(56) References Cited

OTHER PUBLICATIONS

Simon B. Laughlin and Terrence J. Sejnowski, HHMI Howard Hughes Medical Institute, Published as: Science. Sep. 26, 2003; 301 (6541): pp. 1870-1874.
Brian Blais, Leon N. Cooper, Harel Shouval, Formation of Direction Selectivity in Natural Scene Environments, Neural Computation, vol. 12, Issue 5, pp. 1057-1066, May 2000.
Allen Institute for Brain Science, Allen Institute for Brain Science Launches New Atlas Resource and Enhances Others With New Data and Tools, Nov. 14, 2008, from http://alleninstitute.org/content/Press/2008_1114_PressRelease_DataRelease.pdf.
Andrillon T, Nir Y, Staba RJ, Ferrarelli F, Cirelli C, Tononi G, Fried I. Sleep spindles in humans: insights from intracranial EEG and unit recordings. J Neurosci. Dec. 7, 2011;31(49):17821-34. doi: 10.1523/JNEUROSCI.2604-11.2011. PMID: 22159098; PMCID: PMC3270580.
Green AL, Wang S, Stein JF, Pereira EA, Kringelbach ML, Liu X, Brittain JS, Aziz TZ. Neural signatures in patients with neuropathic pain. Neurology. Feb. 10, 2009;72(6):569-71. doi: 10.1212/01.wnl. 0000342122.25498.8b. PMID: 19204269; PMCID: PMC2818184.
Lundqvist, A., Liljander, V., Gummerus, J. and van Riel, A. (2013), "The impact of storytelling on the consumer brand experience: the case of a firm-originated story", Journal of Brand Management 20, 283-297.
Uhlhaas, Peter & Roux, Frédéric & Singer, Wolf & Haenschel, Corinna & Sireteanu, Ruxandra & Rodriguez, Eugenio. (2009). The development of neural synchrony reflects late maturation and restructuring of functional networks in human. Proceedings of the National Academy of Sciences of the United States of America. 106. 9866-71. 10.1073/pnas.0900390106.
Lalkhen, Abdul and Anthony McCluskey. "Clinical tests: sensitivity and specificity." Continuing Education in Anaesthesia, Critical Care & Pain 8 (2008): 221-223.
Hipp, Joerg & Hawellek, David & Corbetta, Maurizio & Siegel, Markus & Engel, Andreas. (2012). Large-scale cortical correlation structure of spontaneous oscillatory activity. Nature neuroscience. 15. 884-90. 10.1038/nn.3101.
Uhlhaas PJ, Pipa G, Lima B, Melloni L, Neuenschwander S, Nikolić D, Singer W. Neural synchrony in cortical networks: history, concept and current status. Front Integr Neurosci. Jul. 30, 2009;3:17. doi: 10.3389/neuro.07.017.2009. PMID: 19668703; PMCID: PMC2723047.

\* cited by examiner

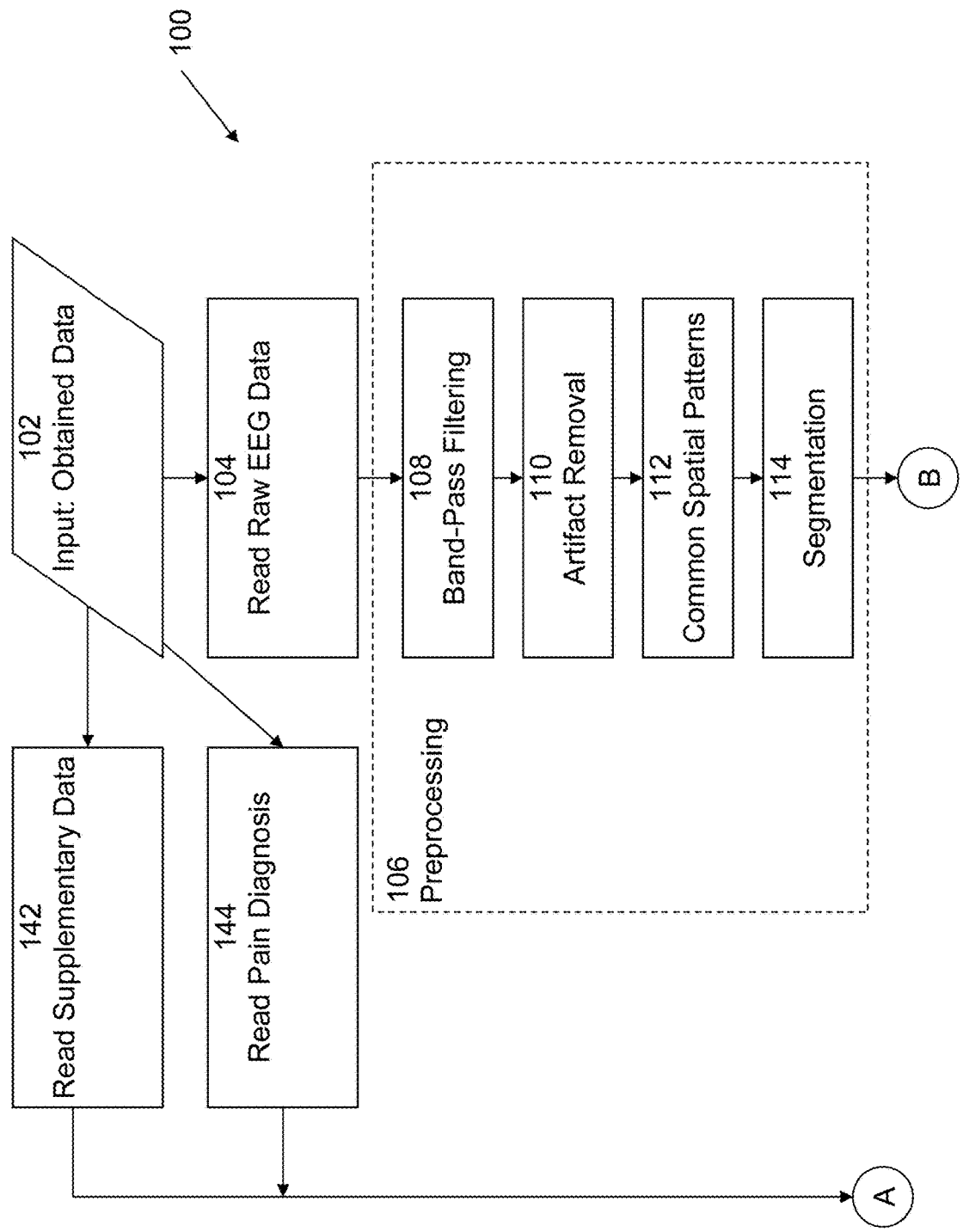

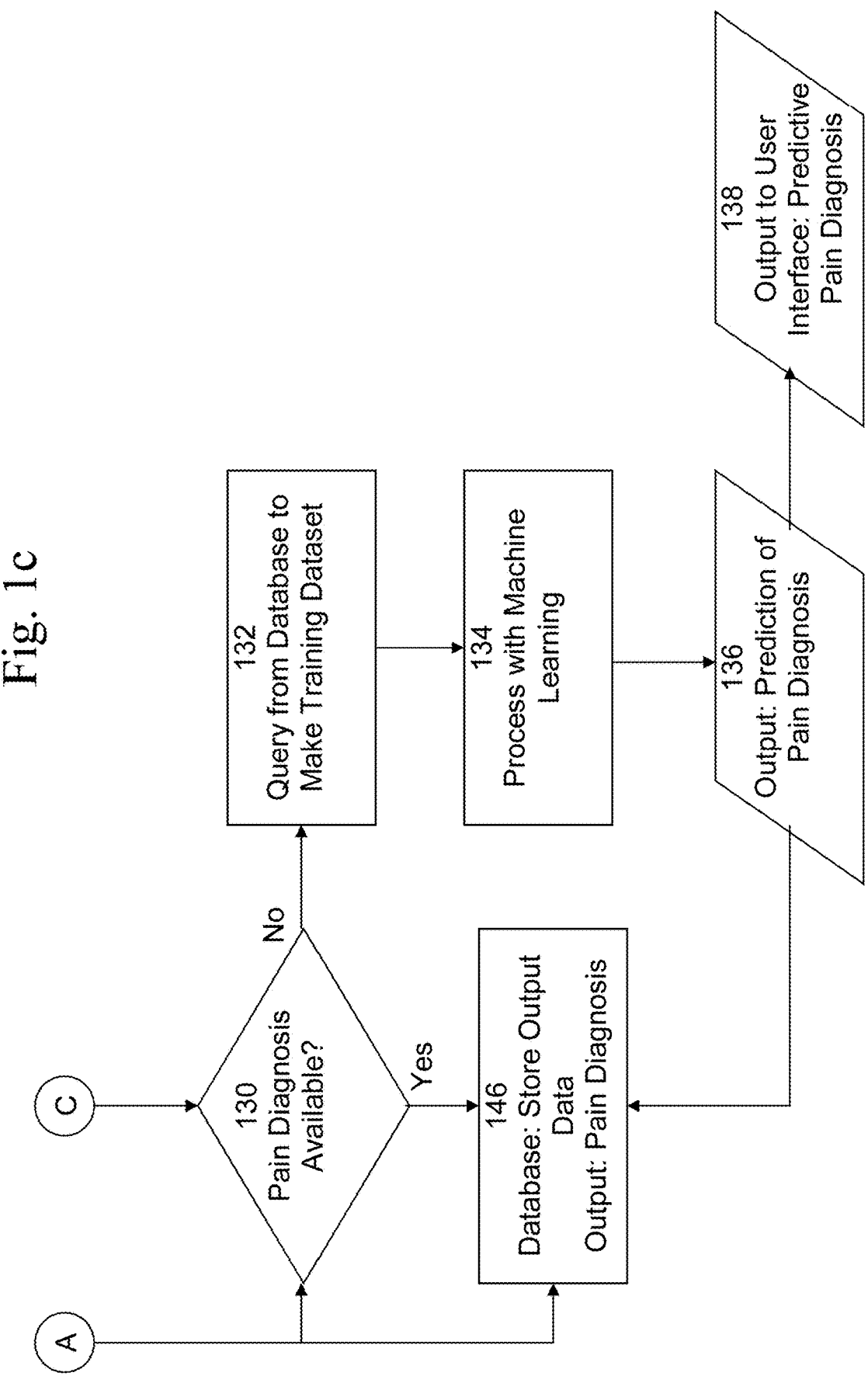

Personalized Fitness Example

Neural Oscillations Monitoring System Algorithm→Classification based on Borg Rating of Perceived Exertion→Scaling a Running-based Training Module

NEURAL OSCILLATION MONITORING SYSTEM

CROSS-REFERENCE TO RELATED APPLICATIONS

This application claims the benefit of U.S. Provisional Application No. 62/214,443, filed Sep. 4, 2015, the entirety of which is incorporated herein by reference. U.S. Pat. No. 9,399,144 is incorporated herein by reference in its entirety.

BACKGROUND

The present invention relates to a neural oscillation monitoring system for objective detection of electrophysiological patterns for various brain functions and dysfunctions.

The methods and mechanisms by which the brain processes information that reflects human behavior is still unclear. With new tools and analysis techniques, researchers are beginning to understand the brain's functions. One way that the information processing occurs in the brain is through brain waves or neural oscillations. Neural oscillations throughout the brain carry a wealth of information about brain function and dysfunction. Neural oscillations have long been correlated to a variety of normal brain functions, ranging from motor control, learning and memory, consciousness, to sleep (Uhlhaas et al 2009). Neural oscillations typically establish great precision in temporal correlations in neural networks and therefore changes or disruptions in these temporal correlations are associated with brain states and in some cases candidate mechanisms of neurological disorders. Therefore it is important to utilize neural oscillations as an accessible pattern of brain function.

The oscillations are often measured using electroencephalography (EEG), as this tool has high temporal resolution, is inexpensive, and the apparatus is easy to wear. Due to the ongoing growth of both large-scale and small-scale interest in self-monitoring, many innovators are interested in developing tools for assessing biological systems and conditions. These products exist in a variety of forms. For example, medical technologies strive to detect biological metrics and convert them into readable and objective scales, while wearable technologies are being used to track physical activity in athletes. However the challenge is to convert a standard EEG data acquisition and analysis system to be used for brain and body self-awareness and dynamic motion.

EEG signals recorded from the brain are typically raw signals that carry uninteresting signals in addition to the interesting patterns, as well as noise. Pre-processing or cleaning and signal processing removes the unwanted signals and artifacts or noise to enable quantification of interesting EEG signals. EEGs are made up of different frequencies and the major frequency bands, delta, theta, alpha, beta, gamma, and sigma-burst, have been well-studied and are associated with specific behaviors such as learning, memory, movement, sleep, etc. Given the wealth of information the brain holds with neural oscillations, a need arises for an automated signal analysis system that can continuously provide up-to-date results that link EEG and behaviors that are important for daily activities.

SUMMARY

Embodiments of the present invention may provide automated techniques for signal analysis that may continuously provide up-to-date results that link EEG and behaviors that are important for daily activities. Such techniques may provide automation, objectivity, real-time monitoring and portability.

In an embodiment of the present invention, a computer-implemented method for monitoring neural activity may comprise receiving data representing at least one signal representing neural activity of a test subject, pre-processing the received data by performing at least one of band-pass filtering, artifact removal, identifying common spatial patterns, and temporally segmentation, processing the pre-processed data by performing at least one of time domain processing, frequency domain processing, and time-frequency domain processing, generating a machine learning model using the processed data as a training dataset, and outputting a characterization of the neural activity based on the machine learning model.

In an embodiment, the artifact removal may comprise determining signals representing a plurality of nearest neighbors of the at least one signal and generating a weighted average of the signals of the plurality of nearest neighbors. The identifying common spatial patterns may comprise selecting signals that shown a highest variance. The time domain processing may comprise performing spindle threshold analysis by setting a threshold at a maximum value, reducing the threshold repeatedly until the threshold is at a minimum value and detecting a spindle when a region of the data exceeds a current threshold value for at least a predetermined amount of time. The frequency domain processing may comprise performing power spectrum analysis using a Fourier transform or a fast Fourier transform. The time-frequency domain processing may comprise performing wavelet analysis using a short time Fourier transform or a wavelet transform. The method may further comprise storing data related to the characterization of the neural activity in a database, receiving additional data representing at least one signal representing additional neural activity of the test subject or neural activity of another test subject, accessing the database using the additional data to determine whether a corresponding characterization of the neural activity is found in the database, when a corresponding characterization of the neural activity is found in the database, outputting the corresponding characterization of the neural activity found in the database.

In an embodiment of the present invention, a computer program product for monitoring neural activity may comprise a non-transitory computer readable storage having program instructions embodied therewith, the program instructions executable by a computer, to cause the computer to perform a method comprising receiving data representing at least one signal representing neural activity of a test subject, pre-processing the received data by performing at least one of band-pass filtering, artifact removal, identifying common spatial patterns, and temporally segmentation, processing the pre-processed data by performing at least one of time domain processing, frequency domain processing, and time-frequency domain processing, generating a machine learning model using the processed data as a training dataset, and outputting a characterization of the neural activity based on the machine learning model.

In an embodiment of the present invention, a system for determining compliance with a planogram may comprise a processor, memory accessible by the processor, and computer program instructions stored in the memory and executable by the processor to perform receiving data representing at least one signal representing neural activity of a test subject, pre-processing the received data by performing at least one of band-pass filtering, artifact removal, identifying common spatial patterns, and temporally segmentation, processing the pre-processed data by performing at least one of time domain processing, frequency domain processing, and time-frequency domain processing, generating a machine learning model using the processed data as a training dataset, and outputting a characterization of the neural activity based on the machine learning model.

BRIEF DESCRIPTION OF THE DRAWINGS

The details of the present invention, both as to its structure and operation, can best be understood by referring to the accompanying drawings, in which like reference numbers and designations refer to like elements.

FIGS. 1a, 1b, and 1c are an exemplary flow diagram of a process according to an embodiment of the present invention.

DETAILED DESCRIPTION

Figure 1B:
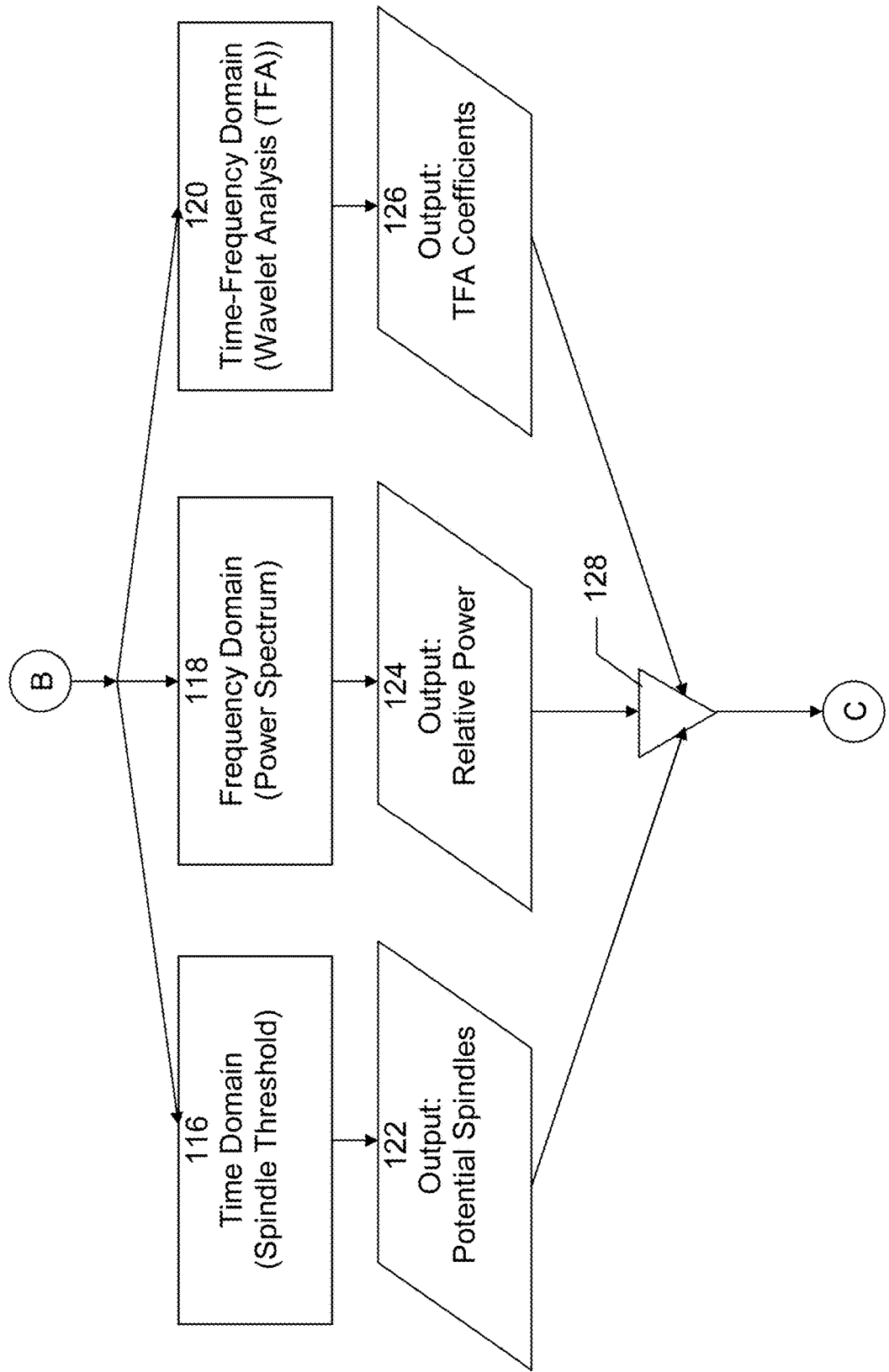

Embodiments of the present invention may provide automated techniques for checking store shelves for compliance with planograms that can handle unknown arrangements in a uniform way, with little user involvement, and with relatively low processing complexity.

For example, embodiments of the present invention may provide a neural oscillation monitoring system. The monitoring system may be configured to receive, process, detect, and optimize performance for a wide range of activities that may be recorded using electrophysiological monitoring devices. The monitoring system may allow raw EEG signals measured from a human to be inputted into the system and undergo signal processing. Machine learning may then be used to classify the signals into groups pertaining to subject cohorts. The results of the monitoring system may be utilized for several applications. For example, the results may be used to detect EEG patterns of specific brain functions or dysfunctions such as mood states or neurological disorders and healthy controls. Another example may be utilizing these EEG patterns to optimize fitness training modules.

In an embodiment, the present invention may provide software that is compatible with a variety of off-the-shelf EEG sensors. Another embodiment may provide a software application integrated into a gaming or fitness equipment console for personalized fitness. Another embodiment may provide a software mobile application. Another embodiment may provide a novel EEG sensor that can acquire and analyze/monitor EEG data. Another embodiment may provide a novel EEG sensor that communicates wirelessly with a mobile application neural oscillation monitoring software.

In an embodiment, a neural oscillation monitoring system may provide objective brain function monitoring and may provide results in real-time. Given the automated nature, the invention may be portable in a software or hardware application.

In an embodiment, the present invention may involve input of raw EEG signals, processing, detecting and utilizing the raw EEG signals for a variety of applications. The raw signals may first be pre-processed to remove artifacts and filter the frequencies of interest. The pre-processing may be performed in several ways, such as band-pass filtering, artifact removal by averaging, common spatial pattern processing to select EEG electrodes based on current source/signal localization, and segmentation of the EEG recordings. A variety of different signal processing tools may be utilized, and analysis in the three domains of EEG signals is shown as examples. In the time domain, spindle threshold analysis may be performed. In the frequency domain, power spectrum analysis may be performed. In the time-frequency domain, wavelet analysis may be performed. Features from these signal processing steps may be selected based on EEG signals or biomarkers of interest and may be used in machine learning. Several machine learning tools may be employed, such as nearest neighbors, support vector machines (SVM), and naive Bayes.

An example of a process 100 of neural oscillation monitoring is shown in FIGS. 1a, 1b, and 1c. For simplicity, process 100 is described using the example of a pain diagnosis. However, this is merely an example, as process 100 is equally applicable any neural oscillation based diagnosis or condition. Process 100 may be fully automated and may be trained on EEG data from specified groups. Once trained, process 100 may provide the capability to blindly classify an unknown EEG into groups as defined by the user. The results of the analysis may provide accuracy, sensitivity and specificity of dividing the initial EEG data into cohorts/groups or patterns. The results may be utilized in use-cases such as medical diagnosis, pharmaceutical drug efficacy studies, personalized fitness consumer use, and others.

Process 100 begins with 102, shown in FIG. 1a, in which input data may be obtained. Data may be input into algorithm in several forms, for example, text files, real-time raw data through software development kits, real-time raw neural oscillations or EEG data, etc. For example, at 104, raw EEG data files may be read. As an example, documented Python functions may be used for monitoring systems that use Python scripts. The listed techniques are merely examples; the present invention contemplates data input in any format using any input technique.

At 106, preprocessing may be performed on the obtained data, such as the raw EEG data. Typically, raw EEG data, which may include EEG data obtained directly from EEG recording equipment, requires pre-processing and cleaning. For example, at 108, band-pass filtering may be performed. Band-Pass filtering may include frequency filtering the data in order to analyze neural oscillation frequencies of interest. For example, data may be filtered at 4-45 Hz for the complete spectrum (Hipp, et al. 2012) and 8-14 Hz for the broad alpha range (Lundqvist, et al. 2013). At 110, artifact removal may be performed. After filtering of the data, artifact removal may be performed, for example, using an averaging technique such as a linear (nearest neighbor) approach using weighted averaging. Omitting the data from EEG electrodes with artifacts is not a desirable due to the fact that source localization depends on scalp potential distribution. In the linear method, artifacts may be reconstructed through a weighted average of data from neighboring electrodes. The weights may be proportional to the Euclidean distance between the electrodes. For example, the three nearest neighbors of each electrode may be determined and the recordings of the three nearest electrodes may be averaged.

At 112, common spatial pattern (CSP) recognition may be performed. CSP may be used for electrode selection, in order to optimize the data analysis by preselecting those EEG electrodes that show the highest variance in their signal, as these are presumed to reflect a brain function/dysfunction pattern. The CSP processing may provide indications of the electrodes that may contain the best features for classification. This approach reduces the computational requirements during further processing, as only the highest-ranking electrodes may be used for further analysis.

At 114, after CSP processing, segmentation of the data may be performed. A recording may be segmented into short duration intervals, with or without overlapping data points.

Turning now to FIG. 1b, the pre-processed data may be analyzed using a variety of different methods. For example, spindle threshold analysis 116, power spectrum analysis 118, and wavelet analysis 120, as well as other techniques, may be used. These processing methods may be used to identify features for the machine learning.

At 116, spindle threshold analysis in the time domain may be performed. In order to detect pain spindles that may constitute a brain function pattern, a modified spindle amplitude threshold-setting method may be used. In this method, the maximum amplitude in the duration of the recording may be determined using a threshold. Typically, the level of the threshold may be initially set at a maximum value and then may be reduced until the threshold is at zero. For example, the threshold in steps of 10% of the initial amplitude until the threshold of 0 μV is reached. A spindle may be detected when a region of 0.5 seconds of the recording exceeds the current threshold level. At 122, the detected potential spindles may be output.

At 118, power spectrum analysis in the frequency domain may be performed. Power decomposition may be performed to determine the power of each frequency that is contained in the recording by using, for example, fast Fourier transforms (FFT) to decompose the recording into frequencies. Several segments of the EEG data may be averaged in order to reduce the variance of the estimate. At 124, the determined relative power spectra may be output.

At 120, wavelet analysis in the time-frequency domain may be performed. Wavelet/TFA analysis may be performed executed using, for example, a short time Fourier transform or wavelet transform. Time may be mapped into frequency and phase by the Fourier transform and time may be mapped into scale and time for the wavelet transform. A variety of wavelet analyses may be performed. For example, Morlet wavelet analysis provides wavelets that have a sinusoidal shape weighted by a Gaussian kernel and may capture local oscillatory components in a time-series. At 126, the determined coefficients may be output.

At 128 the detected potential spindles, the determined relative power spectra, and the determined TFA coefficients may be combined into a dataset.

Turning now to FIG. 1c, at 130, it may be determined whether or not a pain diagnosis is available in a database (discussed further below) on the basis of the combined dataset. If not, then at 132, a query may be made from the database to generate a training dataset for machine learning. At 134, the training dataset may be processing with machine learning. The goal of the machine learning method is to correctly classify with high accuracy, sensitivity, and specificity, an automated and objective method to classify brain function/dysfunction. Features may be selected as spindles, relative power, and wavelet coefficients. Examples of machine learning techniques that may be used include Naïve Bayes, 1 and 2 Nearest Neighbors, and Support Vector Machine (SVM), as well as other machine learning techniques. Features may be selected from signal processing methods such as potential spindles, relative power, TFA or wavelet coefficients, etc. At 136, a prediction of a pain diagnosis may be output from the machine learning processing. At 138, the prediction of the pain diagnosis may be output in a human readable form on a user interface or other technique for use by a user, doctor, patient, or other person.

In addition, at 140, data related to the prediction of the pain diagnosis may be stored in the database. This database may store information such as raw EEG data, pre-processed EEG data, potential spindle data, relative power spectra data, TFA coefficient data, machine learning data, prediction data, etc. Accordingly, at 142, supplementary data, and, at 144, pain diagnosis data, may be read from the input obtained data 102. These data, as well as other data from the database may be used at 130 to determine whether or not a pain diagnosis is available. As discussed above, if a pain diagnosis is not available, then the dataset may be processed using machine learning. If, at 130, a pain diagnosis is available, then, at 146, the relevant data from the dataset may be stored in the database, and the determined pain diagnosis may be output.

A cross validation technique may be used to evaluate the performance of the classification. For example, a 10-fold cross validation approach may be applied to the dataset to determine sensitivity, specificity and accuracy. The sensitivity of a clinical test refers to the ability of the test to correctly identify those subjects with an EEG pattern of interest or brain state (Lalkhen and McCluskey 2008).

$$\text{Sensitivity} = \frac{\text{True positives}}{\text{True positives} + \text{False negatives}}$$

A test with 100% sensitivity correctly identifies all subjects in a specific brain state. The specificity of a clinical test refers to the ability of the test to correctly identify subjects without the specific brain state (Lalkhen and McCluskey 2008).

$$\text{Specificty} = \frac{\text{True negatives}}{\text{True negatives} + \text{False positives}}$$

A test with 100% specificity correctly identifies all subjects without a specific brain state. The accuracy may be computed by $$\text{Accuracy} = \frac{(\text{True positives} + \text{True negatives})}{\left(\begin{array}{c}\text{True positives} + \text{True negatives} + \\ \text{False positives} + \text{False negatives}\end{array}\right)}$$

The accuracy provides a selection criterion upon which the optimal number of electrodes and best performing algorithm could be determined.

The end results of process 100 may be presented in a variety of ways. One example may be a diagnosis of a brain dysfunction state such as chronic pain or Alzheimer's disease. Another example may be utilizing the real-time accuracy results for applications such as input into personalize fitness-training modules.

Figure 2:
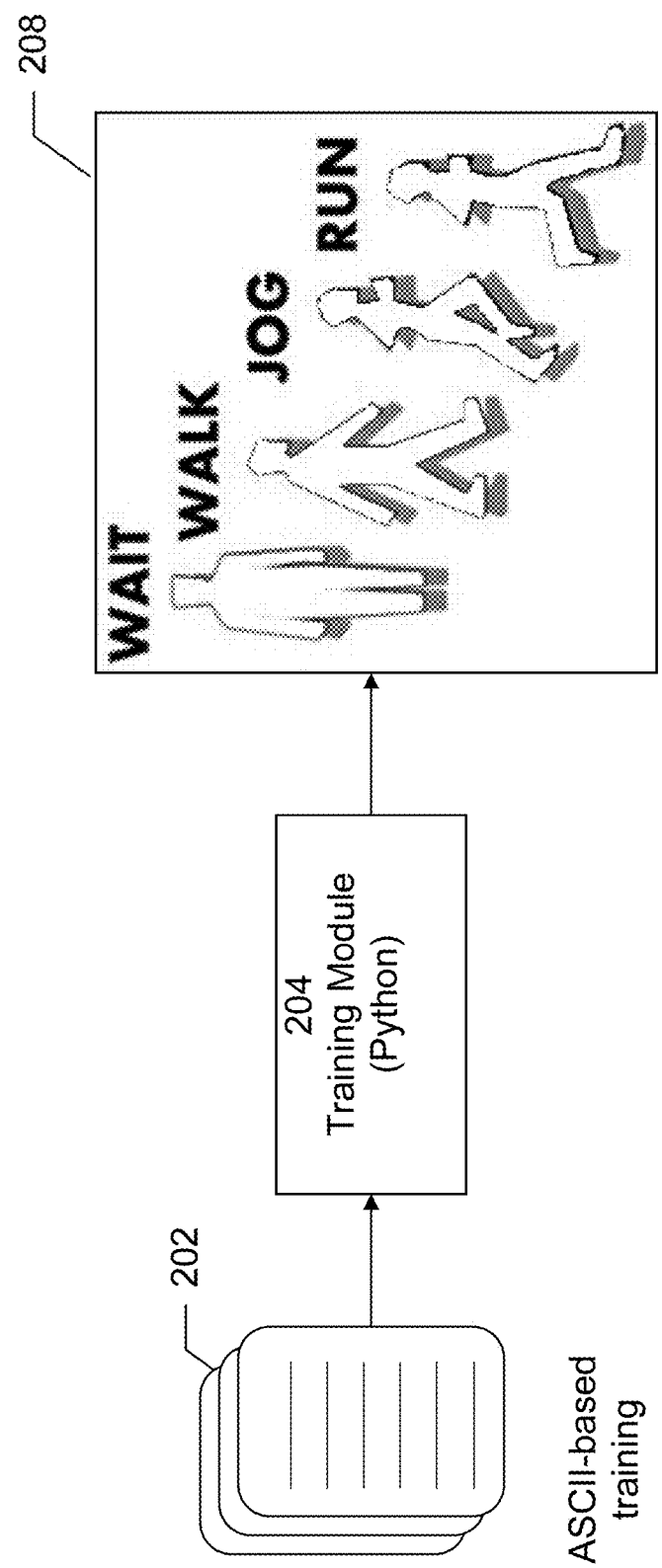
FIG. 2 is an exemplary flow diagram of an application according to an embodiment of the present invention.

An example of the use of neural oscillation monitoring for personalized fitness is shown in FIG. 2. In this example, for each type of exercise or physical activity, EEG data may be collected and compared to non-activity or different modes of activity. For example, EEG data may be collected for running modes: standing, walking, jogging, running. This data may be in any form, but in the example shown in FIG. 2, the data may include ASCII-based training data 202. The EEG patterns associated with the body's response to these modes may be measured and used to train the neural oscillation monitoring system, for example, using the illustrated Python-based training module 204. For example, if an exerciser is experiencing high levels of exertion, discomfort, or pain in the jogging mode, this data may then be used to train the monitoring system to learn the level of exertion of the mode 208. For example, the results of the neural oscillation detection may be represented in the BORG scale for physical exertion. The results of the EEG-BORG scale may then be used to scale an exercise-training module. This may allow the exerciser to personalize their running based on their body's exertion levels. Accordingly, in this example, an exerciser may personalize their training to their body's requirements for an effective workout.

Figure 3:
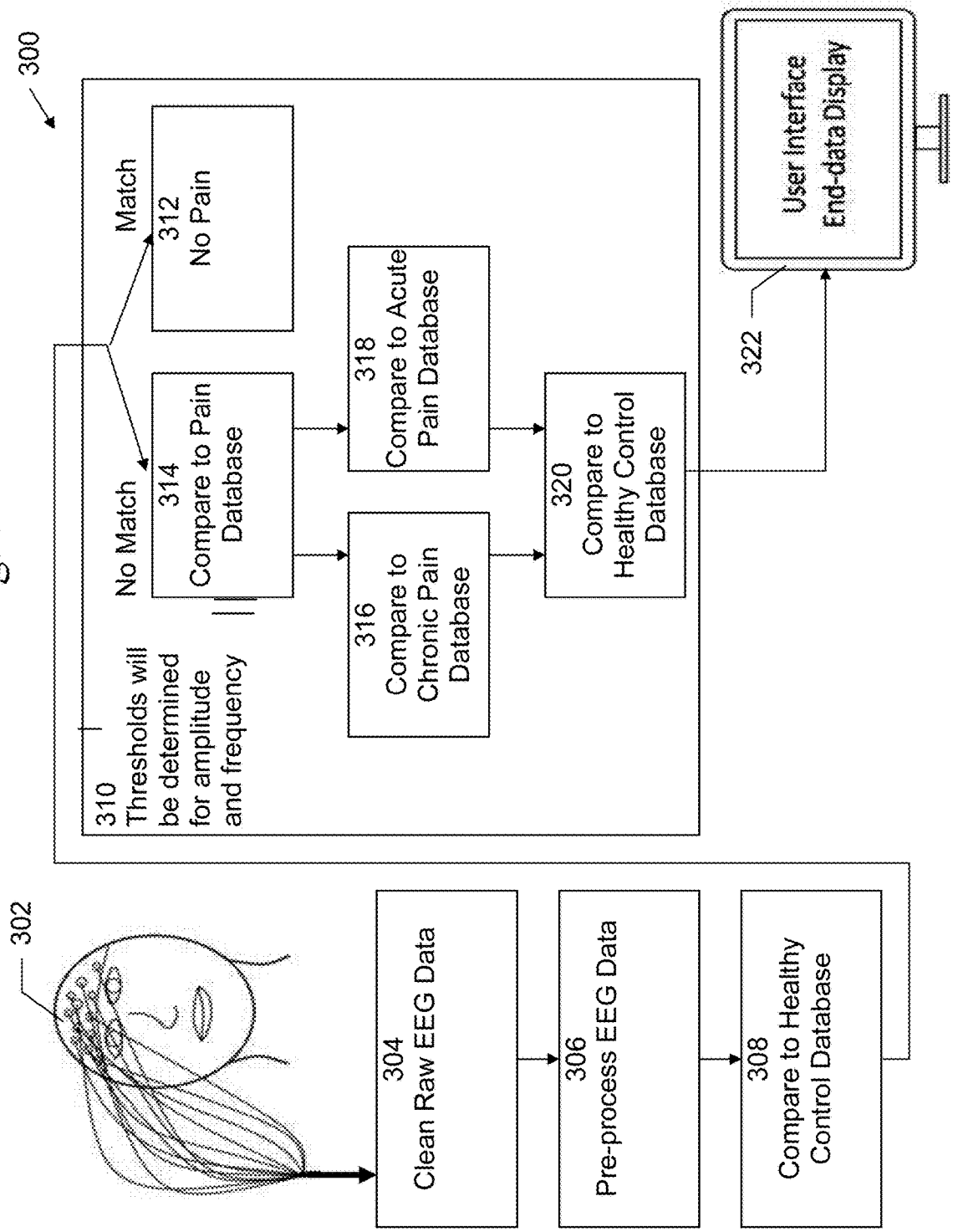
FIG. 3 is an exemplary diagram of an application according to an embodiment of the present invention.

An example of the use of neural oscillation monitoring for pain diagnosis is shown in FIG. 3. Chronic pain is a severe and growing problem in the United States, affecting 116 million Americans and costing $635 billion annually. Pain is especially a significant problem for the military, as a high percentage of soldiers and veterans suffer from both acute and chronic pain. Current pain diagnosis relies on subjective self-reporting of patients making it difficult to quantify pain and its intensity. An objective assay that can rapidly and reliably detects or diagnose pain and its intensity would be useful, and would be especially useful for patients that are unable to self-report such as traumatically injured including the cognitively impaired and sedated patients. An objective pain signature associated specifically with chronic neuropathic pain and its intensity level in patients was recently discussed (Green et al 2009). This pain signature is an increase in (alpha) frequency power with greater spindle activity, which was measured using surgically implanted deep brain electrodes. Using the neural oscillation detection algorithm, used EEG may be used for detection of the scalp correlates of the pain signature to enable its use in portable, user-friendly technology. The detection algorithm could classify pain patients from no-pain with 96% accuracy and high pain from low-pain with 100% accuracy based on patient's EEGs.

As shown in FIG. 3, a system 300 for neural oscillation monitoring for pain diagnosis may include EEG data sensors 302, processing and data blocks 304-320, and display device 322. EEG data sensors 302 may be used for gathering raw EEG data from a subject. At processing block 304, the raw EEG data may be cleaned, as described above. At processing block 306, the cleaned EEG data may be pre-processed, as described above. At processing block 308, the cleaned and pre-processed EEG data may be compared to data in a database including corresponding data gathered from healthy control subjects. At processing block 310, thresholds may be determined for amplitude and frequency. If, at 308, it was determined that there was a match between the processed EEG data and one or more entries in the healthy control database, then at 312, it may be determined that the subject does not have pain. If, at 308, it was determined that there was not a match between the processed EEG data and any entries in the healthy control database, then at 314, the processed EEG data may be compared to a pain database, including, at 316, a comparison to a chronic pain database, and at 318, a comparison to an acute pain database. At 320, the processed EEG data, along with data relating to matches of the processed EEG data to the pain database, the chronic pain database, and the acute pain database, may be compared to the healthy control database. At 322, the resulting pain diagnosis may be output or displayed, for example, on a user interfaces.

Figure 4:
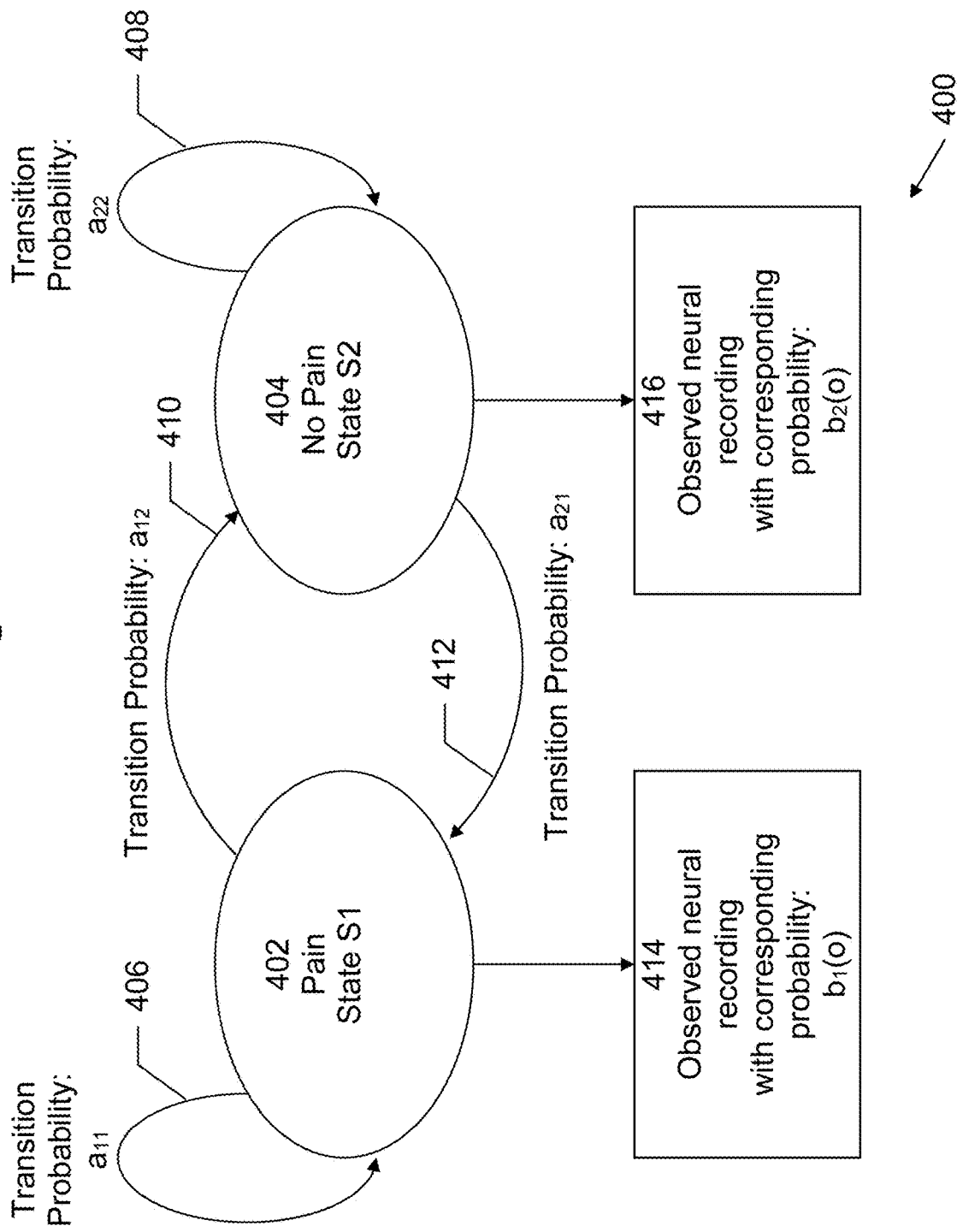
FIG. 4 is an exemplary state diagram of finite state machine processing for an exemplary biomarker pathway that may be performed according to an embodiment of the present invention.

It may be noted that the processing performed at 306, 308, 316 and 318, and 320 may provide input to, or be considered to be steps in finite state machine (FSM) processing. A state diagram 400 of such finite state machine processing for an exemplary biomarker pathway is shown in FIG. 4. As shown in this example, there are two states Pain State S1 402 and No Pain State S2 404. The probability of transition from S1 to S1 is $a_{11}$ 406, the probability of transition from S2 to S2 is $a_{22}$ 408, the probability of transition from S1 to S2 is $a_{12}$ 410, and the probability of transition from S2 to S1 is $a_{21}$ 412. The output 414 from S1 is an observed neural recording with corresponding probability: $b_1(o)$, and output 416 from S2 is an observed neural recording with corresponding probability: $b_2(o)$.

Figure 5:
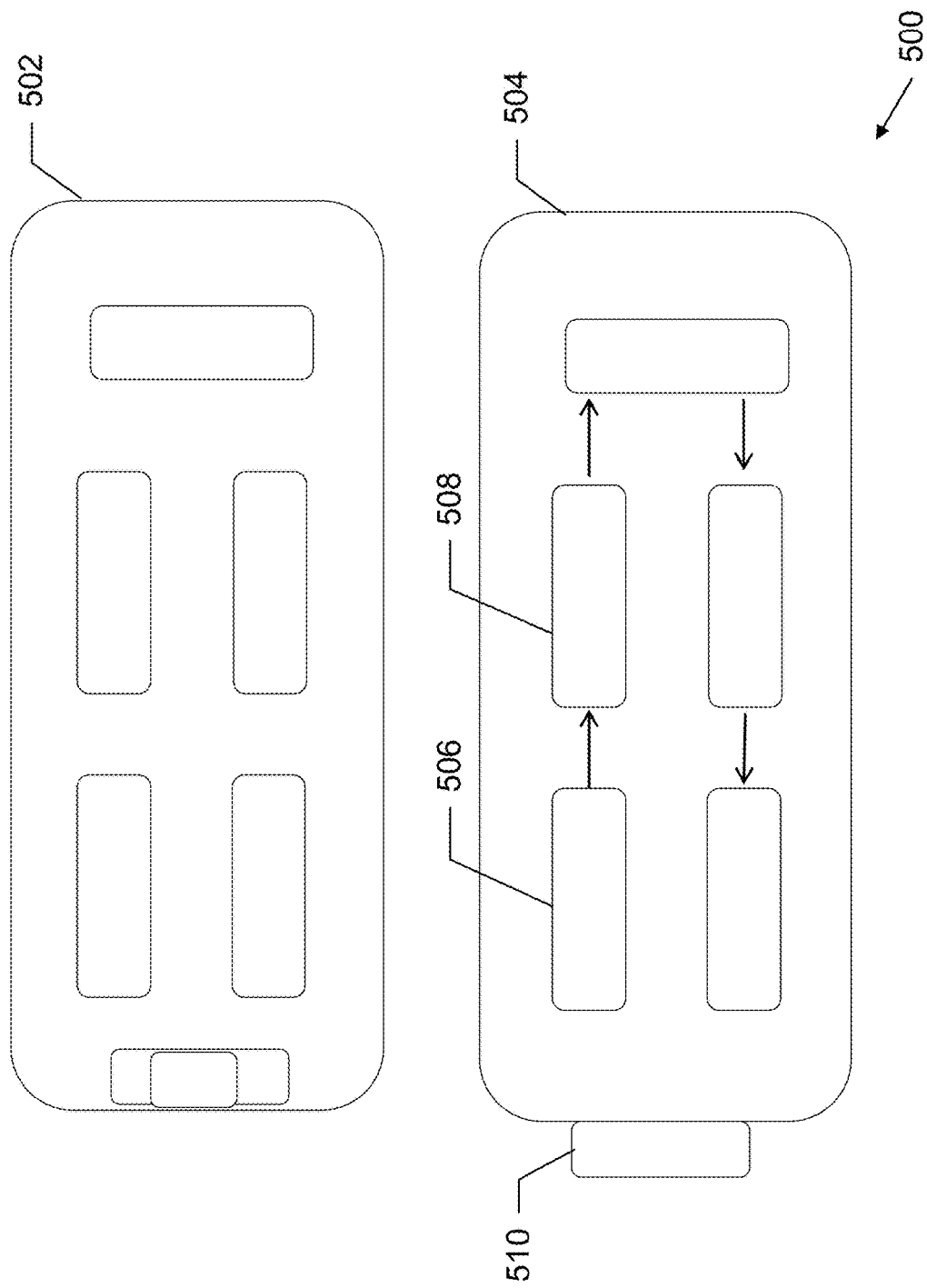
FIG. 5 is an exemplary block diagram of a portable neural oscillation detection system.

An example of a portable neural oscillation detection system 500 is shown in FIG. 5. In this example, a smartphone or other portable or mobile computing device may be utilized as the basis for system 500. For example, a user interface 502, such as a diagnosis and treatment user interface, may be displayed, typically on the front of device 500. User interface 502 may provide the capability to receive input from a user and to display diagnosis and treatment information to the user. On the back 504 of the device, there may be a number of sensor nodes attached to device 500. For example, there may be one or more EEG sensor nodes 506 or electrodes, for detecting EEG signals, as well as one or more transcranial direct-current stimulation (tDCS) nodes 508 or electrodes for providing neurostimulation signals. Further, software 510 to implement the user interface, processing, and signal generation functionality may be provided. Accordingly, this example may be utilized for neural oscillation biomarker detection of pain and provision of tDCS or USN pain treatment signals.

Figure 6:
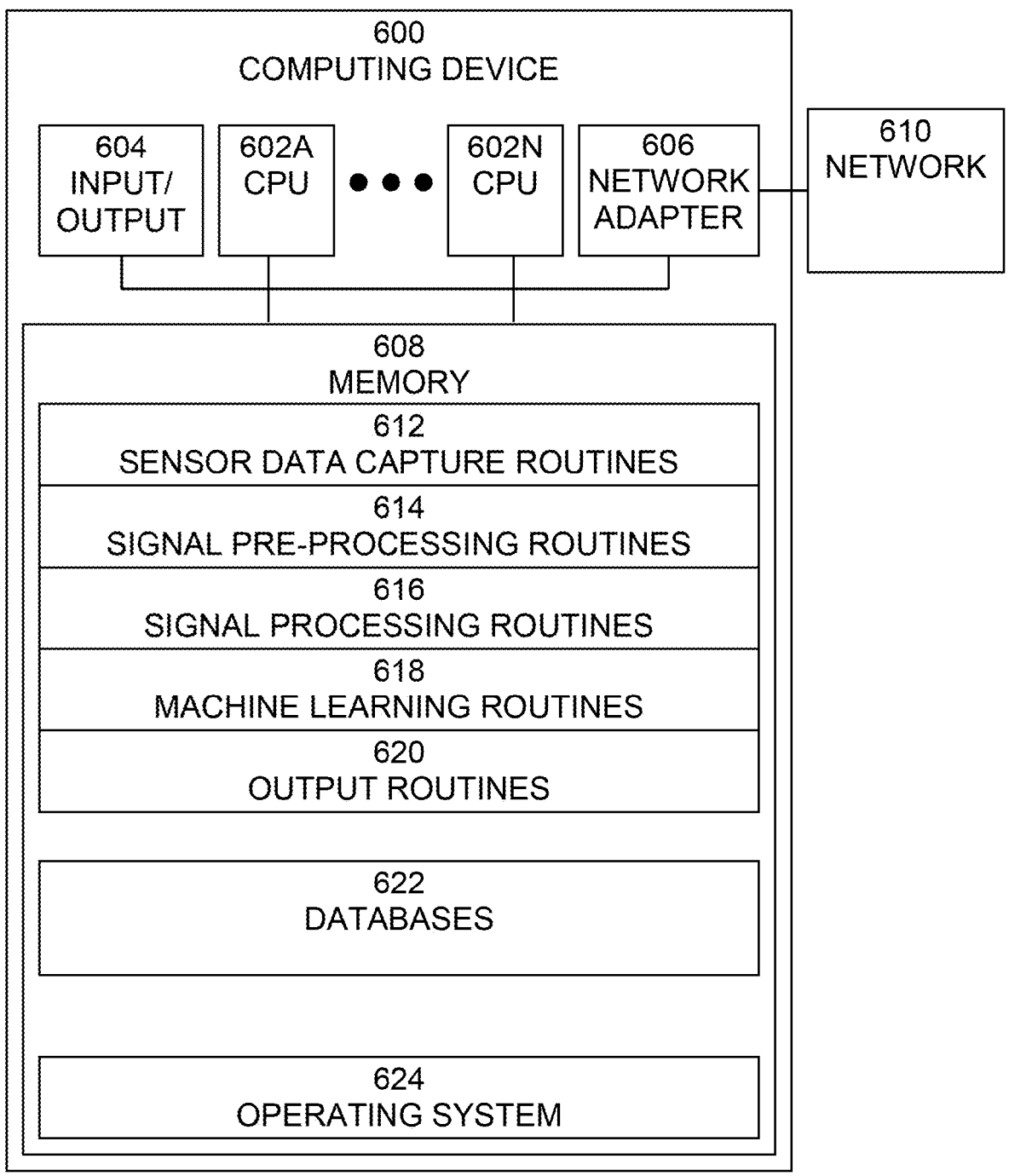
FIG. 6 is an exemplary block diagram of a computing device in which processes involved in the embodiments described herein may be implemented.

An exemplary block diagram of a computing device 600, in which processes involved in the embodiments described herein may be implemented, is shown in FIG. 6. Computing device 600 may be a programmed general-purpose computer system, such as an embedded processor, system on a chip, smartphone, tablet, or other mobile computing device, personal computer, workstation, server system, and minicomputer or mainframe computer. Computing device 600 may include one or more processors (CPUs) 602A-602N, input/output circuitry 604, network adapter 606, and memory 608. CPUs 602A-602N execute program instructions in order to carry out the functions of the present invention. Typically, CPUs 602A-602N are one or more microprocessors, such as an INTEL PENTIUM® processor. FIG. 6 illustrates an embodiment in which computing device 600 is implemented as a single multi-processor computer system, in which multiple processors 602A-602N share system resources, such as memory 608, input/output circuitry 604, and network adapter 606. However, the present invention also contemplates embodiments in which computing device 600 is implemented as a plurality of networked computer systems, which may be single-processor computer systems, multi-processor computer systems, or a mix thereof.

Input/output circuitry 604 provides the capability to input data to, or output data from, computing device 600. For example, input/output circuitry may include input devices, such as keyboards, mice, touchpads, trackballs, scanners, etc., output devices, such as video adapters, monitors, printers, etc., and input/output devices, such as, modems, etc. Network adapter 606 interfaces device 600 with a network 610. Network 610 may be any public or proprietary LAN or WAN, including, but not limited to the Internet.

Memory 608 stores program instructions that are executed by, and data that are used and processed by, CPU 602 to perform the functions of computing device 600. Memory 608 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 608 may vary depending upon the function that computing device 600 is programmed to perform. For example, as shown in FIG. 1, computing devices may perform a variety of roles in the system, method, and computer program product described herein. For example, computing devices may perform one or more roles as end devices, gateways/base stations, application provider servers, and network servers. In the example shown in FIG. 6, exemplary memory contents are shown representing routines and data for all of these roles. However, one of skill in the art would recognize that these routines, along with the memory contents related to those routines, may not typically be included on one system or device, but rather are typically distributed among a plurality of systems or devices, based on well-known engineering considerations. The present invention contemplates any and all such arrangements.

In the example shown in FIG. 6, memory 608 may include sensor data capture routines 612, signal pre-processing routines 614, signal processing routines 616, machine learning routines 618, output routines 620, databases 622, and operating system 624. For example, sensor data capture routines 612 may include routines that interact with one or more sensors, such as EEG sensors, and acquire data from the sensors for processing. Signal pre-processing routines 614 may include routines to pre-process the received signal data, such as by performing band-pass filtering, artifact removal, finding common spatial patterns, segmentation, etc. Signal processing routines 616 may include routines to process the pre-processed signal data, such as by performing time domain processing, such as spindle threshold processing, frequency domain processing, such as power spectrum processing, and time-frequency domain processing, such as wavelet analysis, etc. Machine learning routines 618 may include routines to perform machine learning processing on the processed signal data. Databases 622 may include databases that may be used by the processing routines. Operating system 624 provides overall system functionality.

As shown in FIG. 6, the present invention contemplates implementation on a system or systems that provide multi-processor, multi-tasking, multi-process, and/or multi-thread computing, as well as implementation on systems that provide only single processor, single thread computing.

Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method comprising at a computer system comprising a processor, memory accessible by the processor, and computer program instructions stored in the memory and executable by the processor:

accessing a plurality of real-time time-series data based on electrophysiological signals of neural activity of a test subject, each electrophysiological signal obtained using one of a plurality of electro-encephalogram (EEG) sensors gathering raw EEG data representing a plurality of different frequencies, signals, patterns, and noise from the test subject;

comparing in real-time each of the plurality of time-series data with others of the time series data to determine those time-series data having a highest variance;

based on the comparison, selecting in real-time, at the computer system, time-series data from at least some sensors of the plurality of sensors that show the highest variance in their signal;

detecting, at the computer system, a brain function pattern from the selected time-series data by at least one of: spindle threshold analysis in the time domain, a power spectrum analysis in the frequency domain, and a wavelet analysis in the time-frequency domain;

determining whether the detected brain function pattern indicates an available pain diagnosis;

based on the determination, when a pain diagnosis is not available, generating an instruction to generate a training database for a machine learning model and training the machine learning model using the training database;

determining whether the time-series data indicates a chronic pain diagnosis or an acute pain diagnosis based on the detected brain function pattern using the trained machine learning model; and outputting the indicated pain diagnosis in a human readable form.

2. The method of claim 1, wherein the spindle threshold analysis in the time domain comprises
setting a threshold at a maximum value;
reducing the threshold repeatedly until the threshold is at a minimum value; and
detecting a spindle when a region of the data exceeds a current threshold value for at least a predetermined amount of time.

3. The method of claim 2, wherein the power spectrum analysis in the frequency domain comprises performing power spectrum analysis using a Fourier transform or a fast Fourier transform.

4. The method of claim 3, wherein the wavelet analysis in the time-frequency domain comprises performing wavelet analysis using a short time Fourier transform or a wavelet transform.

5. The method of claim 1, further comprising:
storing data related to the characterization of the neural activity in a database;
receiving additional data representing at least one signal representing additional neural activity of the test subject or neural activity of another test subject;
accessing the database using the additional data to determine whether a corresponding characterization of the neural activity is found in the database; and
when a corresponding characterization of the neural activity is found in the database, outputting the corresponding characterization of the neural activity found in the database.

6. The method of claim 1, further comprising:
before the comparing, processing each of the plurality of time-series data to perform:
cleaning the raw EEG data from each EEG sensor to remove unwanted signals and noise to form cleaned EEG data from each sensor;
band-pass filtering the cleaned EEG data from each sensor at the computer system by frequency filtering the cleaned EEG data from each sensor to analyze neural oscillation frequencies to obtain a filtered EEG data from each sensor including neural oscillation frequencies; and
removing, at the computer system, artifacts from the filtered EEG data from each sensor by averaging the filtered EEG data from each sensor with filtered EEG data from at least one other sensor.

7. A computer program product for monitoring neural activity, the computer program product comprising a non-transitory computer readable storage having program instructions embodied therewith, the program instructions executable by a computer, to cause the computer to perform a method comprising:
at the computer system comprising a processor, memory accessible by the processor, and computer program instructions stored in the memory and executable by the processor, a digital signal representing neural activity of a test subject, accessing a plurality of real-time time-series data based on electrophysiological signals obtained using a plurality of electro-encephalogram (EEG) sensors gathering raw EEG data representing a plurality of different frequencies, signals, patterns, and noise from the test subject;
comparing in real-time each of the plurality of time-series data with others of the time series data to determine those time-series data having a highest variance;
based on the comparison, selecting in real-time, at the computer system, time-series data from at least some sensors of the plurality of sensors that show the highest variance in their signal;
detecting, at the computer system, a brain function pattern from the selected time-series data by at least one of: spindle threshold analysis in the time domain, a power spectrum analysis in the frequency domain, and a wavelet analysis in the time-frequency domain;
determining whether the detected brain function pattern indicates an available pain diagnosis;
based on the determination, when a pain diagnosis is not available, generating an instruction to generate a training database for a machine learning model and training the machine learning model using the training database;
determining whether the time-series data indicates a chronic pain diagnosis or an acute pain diagnosis based on the detected brain function pattern using the trained machine learning model; and
outputting the indicated pain diagnosis in a human readable form.

8. The computer program product of claim 7, wherein the spindle threshold analysis in the time domain comprises:
setting a threshold at a maximum value;
reducing the threshold repeatedly until the threshold is at a minimum value; and
detecting a spindle when a region of the data exceeds a current threshold value for at least a predetermined amount of time.

9. The computer program product of claim 8, wherein the power spectrum analysis in the frequency domain comprises performing power spectrum analysis using a Fourier transform or a fast Fourier transform.

10. The computer program product of claim 9, wherein the wavelet analysis in the time-frequency domain comprises performing wavelet analysis using a short time Fourier transform or a wavelet transform.

11. The computer program product of claim 7, further comprising program instructions for:
storing data related to the characterization of the neural activity in a database;
receiving additional data representing at least one signal representing additional neural activity of the test subject or neural activity of another test subject;
accessing the database using the additional data to determine whether a corresponding characterization of the neural activity is found in the database; and
when a corresponding characterization of the neural activity is found in the database, outputting the corresponding characterization of the neural activity found in the database.

12. The computer program product of claim 7, further comprising:
before the comparing, processing each of the plurality of time-series data to perform:
cleaning the raw EEG data from each EEG sensor to remove unwanted signals and noise to form cleaned EEG data from each sensor;
band-pass filtering the cleaned EEG data from each sensor at the computer system by frequency filtering the cleaned EEG data from each sensor to analyze neural oscillation frequencies to obtain a filtered EEG data from each sensor including neural oscillation frequencies; and
removing, at the computer system, artifacts from the filtered EEG data from each sensor by averaging the filtered EEG data from each sensor with filtered EEG data from at least one other sensor.

13. A system for monitoring neural activity, the system comprising:
  a processor, memory accessible by the processor, and computer program instructions stored in the memory and executable by the processor to perform:
  accessing a plurality of real-time time-series data based on electrophysiological signals of neural activity of a test subject, each electrophysiological signal obtained using one of a plurality of electro-encephalogram (EEG) sensors gathering raw EEG data representing a plurality of different frequencies, signals, patterns, and noise from the test subject;
  comparing in real-time each of the plurality of time-series data with others of the time series data to determine those time-series data having a highest variance;
  based on the comparison, selecting in real-time, at the computer system, time-series data from at least some sensors of the plurality of sensors that show the highest variance in their signal;
  detecting, at the computer system, a brain function pattern from the selected time-series data by at least one of: spindle threshold analysis in the time domain, a power spectrum analysis in the frequency domain, and a wavelet analysis in the time-frequency domain;
  determining whether the detected brain function pattern indicates an available pain diagnosis;
  based on the determination, when a pain diagnosis is not available, generating an instruction to generate a training database for a machine learning model and training the machine learning model using the training database;
  determining whether the time-series data indicates a chronic pain diagnosis or an acute pain diagnosis based on the detected brain function pattern using the trained machine learning model; and
  outputting the indicated pain diagnosis in a human readable form.

14. The system of claim 13, wherein the spindle threshold analysis in the time domain comprises:
  setting a threshold at a maximum value;
  reducing the threshold repeatedly until the threshold is at a minimum value; and
  detecting a spindle when a region of the data exceeds a current threshold value for at least a predetermined amount of time.

15. The system of claim 14, wherein the power spectrum analysis in the frequency domain comprises performing power spectrum analysis using a Fourier transform or a fast Fourier transform.

16. The system of claim 15, wherein the wavelet analysis in the time-frequency domain comprises performing wavelet analysis using a short time Fourier transform or a wavelet transform.

17. The system of claim 13, further comprising computer program instructions for:
  storing data related to the characterization of the neural activity in a database;
  receiving additional data representing at least one signal representing additional neural activity of the test subject or neural activity of another test subject;
  accessing the database using the additional data to determine whether a corresponding characterization of the neural activity is found in the database; and
  when a corresponding characterization of the neural activity is found in the database, outputting the corresponding characterization of the neural activity found in the database.

18. The system of claim 13, wherein the processor, memory, and computer program instructions are included in a portable or mobile computing device.

19. The system of claim 13, further comprising:
  before the comparing, processing each of the plurality of time-series data to perform:
  cleaning the raw EEG data from each EEG sensor to remove unwanted signals and noise to form cleaned EEG data from each sensor;
  band-pass filtering the cleaned EEG data from each sensor at the computer system by frequency filtering the cleaned EEG data from each sensor to analyze neural oscillation frequencies to obtain a filtered EEG data from each sensor including neural oscillation frequencies; and
  removing, at the computer system, artifacts from the filtered EEG data from each sensor by averaging the filtered EEG data from each sensor with filtered EEG data from at least one other sensor.

* * * * *